United States Patent [19]
Babson et al.

[11] 4,250,041
[45] Feb. 10, 1981

[54] REMOVAL OF HEPARIN FROM BLOOD PLASMA SAMPLES USING AN INSOLUBLE PROTAMINE REACTION PRODUCT

[75] Inventors: Arthur L. Babson, Chester; James E. Turner, Morristown, both of N.J.

[73] Assignee: Warner-Lambert Company, Morris Plains, N.J.

[21] Appl. No.: 51,779

[22] Filed: Jun. 25, 1979

Related U.S. Application Data

[62] Division of Ser. No. 931,033, Aug. 4, 1978, Pat. No. 4,199,502.

[51] Int. Cl.³ .................... A61K 35/16; A61K 49/00; C08B 37/10; G01N 1/00
[52] U.S. Cl. ...................... 252/1; 23/230 B; 210/927; 260/112 B; 260/121; 424/2; 424/9; 424/101; 536/21
[58] Field of Search ............ 536/21; 424/101; 260/112 B, 121; 210/28; 252/1

[56] References Cited

U.S. PATENT DOCUMENTS 4,175,182  11/1979  Schmer .................. 536/21

OTHER PUBLICATIONS

J. Lab. Clin. Med. 34, pp. 473–476 (1949), Allen et al.
Arch. Biochem. Biophys. 126:10–26 (1968), Habeeb et al.
Arch. Biochem. Biophys. 144:394–400 (1971), Jansen et al.
J. Lab. Clin. Med. 48, 223–226 (1956), Perkins.

*Primary Examiner*—Howard E. Schain
*Attorney, Agent, or Firm*—Stephen I. Miller; Walter Patton; Stephen Raines

[57] ABSTRACT

This invention relates to a method for the removal of heparin from heparin-containing plasma test samples using an insoluble protamine reaction product, without adversely affecting subsequent testing of the plasma for clotting time. Protamine sulfate or a combination of protamine sulfate and serum albumin is cross-linked with glutaraldehyde to form an insoluble reaction product which is capable of adsorbing heparin. According to the method of this invention, excess amounts of either of the cross-linked protamine reaction products are added to blood plasma samples containing heparin and the mixture is agitated for a time sufficient to permit adsorption of substantially all heparin present. The insoluble protamine heparin complex formed is removed from the plasma along with any excess insoluble protamine reaction product. Aliquots of the heparin-free plasma may be subjected to coagulation tests in order to determine true clotting time.

8 Claims, No Drawings

REMOVAL OF HEPARIN FROM BLOOD PLASMA SAMPLES USING AN INSOLUBLE PROTAMINE REACTION PRODUCT

This is a division of application Ser. No. 931,033 filed Aug. 4, 1978, now U.S. Pat. No. 4,199,502.

BACKGROUND OF THE INVENTION

1. Field of the Invention

The present invention relates to the removal of heparin from blood plasma test samples.

2. Description of the Prior Art

Heparin is widely used as a parenteral anticoagulant for the treatment of thromboembolic patients, for the prophylactic treatment of high risk embolic patients and to reduce the incidence of deep-vein thrombosis after major surgery. Thromboembolic conditions are characteristic of disease states such as coronary thrombosis, venous thrombosis, pulmonary embolism and the like. During treatment, it is necessary to determine the patient's clotting time in the absence of heparin, i.e., the true blood plasma clotting time. Thus, it is necessary to neutralize or remove the heparin from the sample of the patient's blood plasma prior to coagulation testing.

Conventionally, heparin is neutralized by reaction with protamine, as described by Allen, J. G., et al., "A Protamine Titration as an Indication of a Clotting Defect in Certain Hemorrhagic States", in J. Lab. Clin. Med. 34:473–476 (1949); and by Perkins, H. A., "Neutralization of Heparin In Vitro with Protamine; A Simple Method of Estimating the Required Dose", J. Lab. Clin. Med. 48:223–226 (August, 1956). Polybrene, a synthetic polymerized quaternary ammonium salt, has also been used to neutralize heparin (see Godal, H. C., "A Comparison of Two Heparin Neutralizing Agents: Protamine and Polybrene", Scandinav. J. Clin. & Lab. Invest. 12:466–457, (1960).

While the above-mentioned procedures have been used successfully, a tedious titration is required since protamine and polybrene are soluble in plasma. Any excess not combined with heparin will remain in the plasma, frequently undetected, and interfere with the coagulation test. Thus, the accuracy of the coagulation test itself is questionable.

The reaction of glutaraldehyde with various proteins to give soluble and insoluble products has been reported by A. Habeeb, et al. in Arch. Biochem. Biophys. 126:10–26 (1968); and by E. Jansen, et al. in Arch. Biochem. Biophys. 144:394–400 (1971). Neither of these studies discloses the reaction of glutaraldehyde with protamine.

In view of the deficiences of the conventional art methods, there is a need for a simple, rapid procedure for removal of heparin from blood plasma samples without adversely affecting subsequent coagulation testing of the plasma samples.

Co-pending application Ser. No. 931,031, filed Aug. 4, 1978 now abandoned by James E. Turner, James R. Butler and Arthur L. Babson, entitled REMOVAL OF HEPARIN FROM BLOOD PLASMA SAMPLES USING TRIETHYLAMINOETHYL CELLULOSE describes a method for removing heparin using fibrous triethylaminoethyl cellulose; and co-pending application Ser. No. 931,032, filed Aug. 4, 1978 now U.S. Pat. No. 4,198,314 by James E. Turner, James R. Butler and Frank W. Goodhart, entitled REMOVAL OF HEPARIN FROM HEPARIN-CONTAINING BLOOD PLASMA SAMPLES USING A TRIETHYLAMINOETHYL CELLULOSE TABLET, describes a microcrystalline cellulose/triethylaminoethyl cellulose table suitable for removing heparin from blood plasma samples.

SUMMARY OF THE INVENTION

A method for removing substantially all heparin from heparin-containing blood plasma samples using an insoluble protamine reaction product is provided. The insoluble protamine reaction product is prepared by cross-linking either protamine sulfate or protamine sulfate and serum albumin with glutaraldehyde at a pH from about 6 to about 12. In use, excess amounts of the insoluble protamine reaction product are added to one milliliter of heparin-containing blood plasma sample. The sample is agitated briefly and an insoluble complex of heparin with either the protamine/glutaraldehyde reaction product or with the protamine/serum albumin/glutaraladehyde reaction product is formed and settles out of the plasma. Aliquots of the remaining blood plasma samples may be tested for true clotting time without interference from heparin or reagents used to remove the heparin.

DESCRIPTION OF THE PARTICULAR EMBODIMENTS

The present invention relates to a method for removing heparin from heparin-containing blood plasma samples without the need for tedious titration procedures. According to the subject invention, an insoluble protamine reaction product prepared by cross-linking either protamine sulfate or protamine sulfate and serum albumin with glutaraldehyde is added to blood plasma samples in excess of the quantity of heparin present. Upon agitation, the solid phase, insoluble protamine reaction product of this invention combines with the heparin in the plasma and the complex formed settles out of the plasma along with any excess insoluble protamine reaction product present. The plasma samples may be centrifuged to aid in the settling out process. Aliquots of the remaining plasma are then subjected to coagulation testing without danger of interference from heparin or excess protamine, since both have been removed.

The insoluble protamine/glutaraldehyde reaction product of this invention is prepared by dissolving from about 1.5 to about 2.5, preferably about 2 grams of protamine sulfate in from about 20 to about 30, preferably about 25 milliliters of distilled water; adding thereto from about 20 to about 30, preferably about 25 milliliters of 0.132 M phosphate buffer ($KH_2PO_4$, $Na_2HPO_4$) pH 9.0, and adjusting the pH to about 9.0, if necessary, with 0.1 N sodium hydroxide; next there is added thereto from about 6 to about 9, preferably about 8 milliliters of a 10% solution of glutaraldehyde in the 0.132 M phosphate buffer and the mixture is incubated at pH 6 to 12, preferably at pH 9, overnight at from about 4° C. to about 10° C. A precipitate of an insoluble protamine/glutaraldehyde reaction product is formed which, after filtration and further processing to powder form, is suitable for use in the heparin removal process of this invention.

In an alternate process for preparing the insoluble protamine reaction product, serum albumin is added to the protamine sulfateglutaraldehyde reaction mixture in order to increase the yield of reaction product without adversely affecting subsequent use of the product in heparin removal. In the alternate process, from about 0.07 to about 0.13, preferably about 0.1 grams of serum albumin and from about 0.7 to about 1.3, preferably about 1 gram of protamine sulfate are dissolved in from about 20 to about 30, preferably about 25 milliliters of distilled water and the pH of the solution is adjusted to about 4.0 with 0.1 N hydrochloric acid; from about 3 to about 7, preferably about 5 milliliters of a 10% aqueous glutaraldehyde solution is added thereto and the pH is adjusted to from about 6 to about 12, preferably to about 11.5 with 0.1 N sodium hydroxide and the reaction mixture is incubated at from about 4° C. to about 10° C. overnight. A precipitate of an insoluble protamine/albumin/glutaraldehyde reaction product is obtained which, after filtration and further processing to powder form, is suitable for use in the heparin removal process of this invention.

It has been found that from about 10 to about 20 mg., preferably about 14 mg. of the above-described insoluble protamine/glutaraldehyde reaction product per milliliter of plasma sample are capable of removing substantially all heparin from the plasma sample without affecting true clotting time. And from about 4 to about 14 mg., preferably about 6.7 mg. of the insoluble protamine/albumin/glutaraldehyde reaction product per milliliter of plasma sample are capable of removing substantially all heparin from the plasma sample without affecting true clotting time.

In use, either the insoluble protamine/glutaraldehyde reaction product or the insoluble protamine/albumin/glutaraldehyde reaction product is added to the blood plasma sample in the amount specified above and the sample is agitated to bring the reaction product in contact with the plasma for a time sufficient to permit adsorption of substantially all heparin in the plasma sample. A heparin complex is formed within the plasma sample as agitation is continued. Typically, agitation is conducted, either continuously or intermittently, for from about 10 to about 20 minutes, preferably for about 15 minutes, to allow complete adsorption of substantially all of the heparin in the plasma sample. Upon cessation of agitation, the insoluble protamine/heparin complex and any excess insoluble protamine reaction product remaining in the plasma sample precipitates out and settles to the bottom. Precipitation is complete within from 2 to 8 minutes, generally about 5 minutes. If desired, the sample may be centrifuged to aid the precipitation process. Aliquots of heparin-free plasma are then removed and subjected to coagulation testing.

The administration of relatively high therapeutic doses of heparin rarely brings about blood levels of more than 2 units of heparin per milliliter of plasma. The addition of either the protamine/glutaraldehyde reaction product (or the protamine/serum-albumin/glutaraldehyde reaction product) in the above stated amounts to a heparin containing plasma sample has been found capable of removing at least 2 units of heparin per milliliter of plasma sample. Therefore, removal of substantially all heparin in a clinical plasma sample is assured.

The following examples are provided to further illustrate the method of this invention:

EXAMPLE 1

Preparation of an Insoluble Protamine/Glutaraldehyde Reaction Product

1. Dissolve 2.0 gm of protamine sulfate in 25 ml. of distilled water.

2. Add 25 ml. of 0.132 M phosphate buffer ($KH_2PO_4$, $Na_2HPO_4$) pH 9.0 to No. 1. Adjust to pH 9.0 if necessary with 0.1 N NaOH.

3. Prepare a 10% solution of glutaraldehyde by adding 4 ml. of 25% glutaraldehyde to 6 ml. of 0.132 M phosphate buffer. Adjust to pH 9.0 if necessary with 0.1 N NaOH.

4. Add 8 ml. of solution No. 3 to solution No. 2. Stir slowly for ten minutes and incubate overnight at 4° C.

5. Remove the precipitate by filtering the solution through a sintered glass funnel and wash the precipitate on the funnel with 1 liter of distilled water.

6. Dry the precipitate by washing the precipitate on the funnel with 100 ml. of 95% ethanol and 100 ml. of acetone. Dry in a vacuum dessicator.

7. Grind up the hard cake with a mortar and pestle until it is reduced to a powder.

EXAMPLE 2

Preparation of an Insoluble Protamine/Serum Albumin/Glutaraldehyde Reaction Product 1. Dissolve 0.1 gm of bovine serum albumin and 1.0 gm of protamine sulfate in 25 ml. of distilled water. Adjust to pH 4.0 with 0.1 N HCl.

2. Prepare a solution of 10% glutaraldehyde by adding 4 ml. of 25% glutaraldehyde to 6 ml. of distilled water.

3. Add 5 ml. of 10% glutaraldehyde to solution No. 1 and adjust to pH 11.5 with 0.1 N NaOH.

4. Incubate at 4° C. overnight.

5. Filter the solution through a sintered glass funnel and wash the precipitate on the funnel with 1 liter of distilled water.

6. Dry the precipitate by washing the precipitate on the funnel with 100 ml of 95% ethanol and 100 ml. of acetone. Dry in a vacuum dessicator.

7. Grind the hard cake in a mortar until it is reduced to powder.

EXAMPLE 3

Removal of Heparin from Blood Plasma Sample Using Example 1, an Insoluble Protamine/Glutaraldehyde Reaction Product 1. Add 1 ml of the patient's plasma to a 10×75 mm plastic test tube.

2. Add 14 mg. of the insoluble protamine/glutaraldehyde reaction product of Example 1 to the test tube.

3. Agitate at room temperature for 10 seconds every 3 minutes over a 15 minute interval.

4. Allow the test tube to stand undisturbed for 5 minutes.

5. Remove appropriate aliquots of plasma for coagulation testing.

EXAMPLE 4

Removal of Heparin from Blood Plasma Sample Using Example 2, an Insoluble Protamine/Serum Albumin/Glutaraldehyde Reaction Product 1. Add 1 ml of the patient's plasma to a 10×75 mm plastic test tube.

2. Add 6.7 mg. of the insoluble protamine/serum albumin/glutaraldehyde reaction product of Example 2 to the test tube.

3. Agitate at room temperature for 10 seconds every 3 minutes over a 15 minute period.

4. Allow the test tube to stand undisturbed for 5 minutes.

5. Remove appropriate aliquots of plasma for coagulation testing.

We claim:

1. A method for removing substantially all heparin from a heparin-containing blood plasma test sample which comprises:
   A. Adding from about 10 to about 20 mg. of the insoluble protamine/glutaraldehyde reaction product prepared by incubating an aqueous solution containing:
      I. From about 1.5 to about 2.5 grams of protamine sulfate;
      II. From about 20 to about 30 milliliters of water;
      III. From about 20 to about 30 milliliters of phosphate buffer; and
      IV. From about 6 to about 9 milliliters of a 10% solution of glutaraldehyde in phosphate buffer;
      at a pH of from about 6 to about 12 and a temperature of from about 4° C. to about 10° C. overnight;
      per milliliter of plasma to the plasma sample;
   B. Agitating (A) until substantially all the heparin present in the plasma sample is adsorbed by and complexed with the insoluble protamine/glutaraldehyde reaction product;
   C. Allowing (B) to stand for a time sufficient to allow precipitation of the free and complexed insoluble protamine/glutaraldehyde reaction product;
   D. Removing the precipitate of (C) from the plasma sample to obtain substantially heparin-free plasma suitable for coagulation testing.

2. A method according to claim 1 wherein, in Step A, about 14 mg. of insoluble protamine/glutaraldehyde reaction product are added.

3. A method according to claim 2 wherein, in Step B, the agitation is conducted for from about 10 to about 20 minutes.

4. A method according to claim 3 wherein, in Step C, the plasma is allowed to stand for from about 2 to about 8 minutes.

5. A method for removing substantially all heparin from a heparin-containing blood plasma test sample which comprises:
   A. Adding from about 4 to about 14 mg. of the insoluble protamine/serum albumin/glutaraldehyde reaction product, prepared by incubating an aqueous solution containing:
      I. From about 0.07 to about 0.13 grams of serum albumin;
      II. From about 0.7 to about 1.3 grams of protamine sulfate;
      III. From about 20 to about 30 milliliters of water; and
      IV. From about 3 to about 7 milliliters of a 10% aqueous glutaraldehyde solution; at a pH of from about 6 to about 12 and a temperature of from about 4° C. to about 10° C. overnight;
      per milliliter of plasma to the plasma sample;
   B. Agitating (A) until substantially all the heparin present in the plasma sample is adsorbed by and complexed with the insoluble protamine/serum albumin/glutaraldehyde reaction product;
   C. Allowing (B) to stand for a time sufficient to allow precipitation of the free and complexed insoluble protamine/serum albumin/glutaraldehyde reaction product; and
   D. Removing the precipitate of (C) from the plasma sample to obtain a substantially heparin-free plasma suitable for coagulation testing.

6. A method according to claim 5 wherein, in Step A, about 6.7 mg. of insoluble protamine/albumin/glutaraldehyde reaction product is added.

7. A method according to claim 6 wherein, in Step B, the agitation is conducted for from about 10 to about 20 minutes.

8. A method according to claim 7 wherein, in Step C, the plasma is allowed to stand for from about 2 to about 8 minutes.

* * * * *